(12) United States Patent
Shahinpoor et al.

(10) Patent No.: US 8,454,691 B2
(45) Date of Patent: Jun. 4, 2013

(54) SURGICAL CORRECTION OF PTOSIS BY POLYMERIC ARTIFICIAL MUSCLES

(76) Inventors: Mohsen Shahinpoor, Bangor, ME (US); David Soltanpour, New York, NY (US)

( * ) Notice: Subject to any disclaimer, the term of this patent is extended or adjusted under 35 U.S.C. 154(b) by 114 days.

(21) Appl. No.: 12/605,374

(22) Filed: Oct. 26, 2009

(65) Prior Publication Data

US 2010/0042146 A1   Feb. 18, 2010

Related U.S. Application Data

(63) Continuation-in-part of application No. 11/318,665, filed on Dec. 24, 2005, now Pat. No. 7,625,404.

(51) Int. Cl.
*A61F 2/14* (2006.01)
*A61F 2/08* (2006.01)
*A61F 2/00* (2006.01)

(52) U.S. Cl.
USPC .................. 623/14.13; 424/427; 424/428

(58) Field of Classification Search
USPC ......... 623/4.1, 14.13, 905; 514/912; 424/427, 424/428
IPC .................................................. A61F 2/14,9/00
See application file for complete search history.

(56) References Cited

U.S. PATENT DOCUMENTS

| | | | | |
|---|---|---|---|---|
| 5,334,629 A | * | 8/1994 | Zirino | 523/137 |
| 6,511,508 B1 | * | 1/2003 | Shahinpoor et al. | 623/4.1 |
| 2006/0287720 A1 | * | 12/2006 | Tse | 623/4.1 |

* cited by examiner

*Primary Examiner* — David Isabella
*Assistant Examiner* — Yashita Sharma
(74) *Attorney, Agent, or Firm* — V. Gerald Grafe

(57) ABSTRACT

A surgical procedure is described for the restoration of eyelid function in individuals suffering from ptosis or upper eyelid droop syndrome that makes a patient unable to voluntarily fully raise an eyelid. The surgical procedure includes implantation and suturing of eye drop (pH) activated and actuated fibrous contractile and expansive artificial muscles such as pH active hydrogels of polyacrylonitrile (PAN) artificial muscles that are surgically implanted and sutured under the superior palpebral conjunctiva in a serpentine parallel configuration with respect to the tarsal (meibomian) glands of the upper eyelid and anchored to the tissues of superior fornix.

10 Claims, 6 Drawing Sheets

SURGICAL CORRECTION OF PTOSIS BY POLYMERIC ARTIFICIAL MUSCLES

CROSS-REFERENCE TO RELATED APPLICATION

This application is a continuation-in-part of U.S. application Ser. No. 11/318,665, filed Dec. 24, 2005, which is incorporated herein by reference.

TECHNICAL FIELD

The present invention is generally related to restoration of eyelid function and correction of ptosis and, in particular, to a surgical method for restoring eyelid function in a ptosis patient.

BACKGROUND OF THE INVENTION

A drooping of the upper eyelid below its normal level resulting in narrowing of the palpebral opening is known in ophthalmology as ptosis. The muscle controlling lid opening is the levator palpebrae superioris and it is innervated by the third cranial nerve (oculomotor nerve). Ptosis may be congenital or acquired. In congenital ptosis the levator palpebrae superioris muscle that elevates the lid is either absent or not well developed. Acquired ptosis, on the other hand, is usually due to either diseases or injuries of the nerves that control the movements of the levator palpebrae superioris muscle. Ptosis may further be classified as myogenic, aponeurotic, neurogenic, mechanical or traumatic.

The treatment of ptosis has traditionally required accurate and consistent evaluation and measurement as well as skillful use of surgical techniques to implement a functional and aesthetic correction. In most cases, surgery has been required to correct a ptotic eyelid. The surgical procedures used generally depend on the severity of ptosis and are described in the following references, each of which is incorporated by reference in its entirety for all purposes: Callahan M, Beard C: Ptosis, 4th ed. Birmingham: Aesculapius, 1990; Dresner S. C.: Further modifications of the Müller's muscle conjunctival resection procedure. Ophthalmic Plast Reconstr Surg 1991; 7:114-122; Dresner S. C.: Minimal ptosis management. In: Kikkawa D. O., ed. Aesthetic Ophthalmic Plastic Surgery. Philadelphia: Lippincott-Raven, 1997:151-162; Older II: Ptosis repair and blepharoplasty in the adult. Ophthalmic Surg 1995; 4:304-308; and Crawford I. S.: Repair of ptosis using frontalis muscle and fascia lata: a 20 year review. Ophthalmic Surg 1977; 8:31-40.

The amount of levator function present generally determines which surgical procedure will be adopted. For minimal ptosis, Müllerectomy or Fasanella-Servat procedures have been used. Levator aponeurotic surgical repair has been used for patients with involutional changes. Frontalis suspension and Whitnall's sling have been used for more severe cases of ptosis.

In the frontalis suspension operation, the eyelid is suspended from the frontalis so that the eyelid is opened when the patient lifts the eyebrow using the frontalis muscle. Tendon tissue from the patient's leg or biocompatible synthetic materials are also used. While this procedure allows the patient to raise the eyebrow to open the eyelid and therefore see from the eye, it suffers from a number of drawbacks. The patient must adapt to the uncommon, tiring and uncomfortable movement of raising the eyebrow to raise the eyelid. Furthermore, the extent to which the patient is able to raise the eyelid varies from procedure to procedure. Essentially, the procedure restores some eyelid function but that function is not natural. This procedure is also a cosmetic failure because of the requirement for the patient to raise his or her eyebrow.

U.S. Pat. No. 5,522,889 to Baker et al. entitled "Apparatus and method for restoring eyelid function," teaches an apparatus to restore eyelid function in a patient unable to voluntarily raise an eyelid. The apparatus includes a spiral torsion spring and pulley arrangement mounted in a housing that is implanted in fixed positions in the superior portion of the orbit of the eye. A wire connects the pulley to the eyelid. A spiral torsion spring provides the necessary spring force in tension to overcome the weight of the eyelid and draw the eyelid open. The natural muscles of eye closure are, however, sufficiently strong to overcome the spring tension thereby playing out wire from the pulley and closing the eye so as to provide normal blinking function. A position setting gear allows the biasing force of the spring to be selectively reduced sufficiently to allow the eye to remain closed for sleep or at other desired times.

SUMMARY OF THE INVENTION

The present invention provides a novel surgical method and apparatus to restore eyelid function to patients suffering from conditions such as ptosis. The present invention comprises a surgical method that overcomes the above-described limitations and disadvantages of the prior art to restore essentially normal eyelid function in patients unable to raise their lid due to a congenital or acquired condition.

The present invention provides an implantable eye drop activated artificial muscle network to take over the function of the levator palpebrae superioris muscle in a relatively simple manner to be readily surgically implantable in the eye yet providing reliable operation over an extended period.

The present invention provides a surgical method, artificial muscles and eye drops for correcting ptosis in a patient whereby the eyelid is moved in a natural motion so as to restore substantially natural eyelid function.

Additional advantages and other novel features of the invention will be set forth in part in the description that follows and in part will become apparent to those skilled in the art upon examination of the following or may be learned with the practice of the invention.

Other advantages and features of the present invention will become apparent to those skilled in the art from the following description wherein there is shown and described a preferred embodiment of the present invention, simply by way of illustration of one of the modes best suited to carry out the invention. Accordingly, the drawings and descriptions will be regarded as not restrictive and only illustrative in nature.

BRIEF DESCRIPTION OF THE DRAWINGS

The accompanying drawings incorporated in and forming a part of the specification, illustrate several aspects of the present invention and together with the description serves to explain the principles of the invention. In the drawings.

Reference will now be made in detail to the present preferred embodiment of the invention, an example of which is illustrated in the accompanying drawing.

DETAILED DESCRIPTION OF THE INVENTION

Figure 1:
FIG. 1 is a schematic front view of a patient suffering from ptosis in one eye.

The current disclosure provides apparatus and methods for correcting ptosis. FIG. 1 shows a patient suffering from ptosis in one eye. As seen in FIG. 1, a typical ptosis manifests itself in the form of upper eyelid droop under normal conditions. Typically, a surgical approach can be implemented to correct the droopy eyelid. According to the present disclosure, an artificial muscle can be surgically implanted into the eyelid. The implant can then be biased in either an open or closed position with application of different biasing means. The biasing means may take the form of different chemical solutions, for example, in the form of eyedrops having different chemical properties such as different acidities.

As will be described in greater detail below, according to one embodiment of the present invention, biocompatible fibrous contractile and expansive ionic polymeric artificial muscles can be surgically implanted and sutured under the superior palpebral conjunctiva and suture anchored to the tissues of the upper superior fornix. The artificial muscles can be sutured in a serpentine network or grid fashion to form a two-dimensional sheet suture anchored under the superior palpebral conjunctiva tissues in a serpentine and parallel configuration with respect to tarsal (meibomian) glands of the eyelid. The muscles can be further suture anchored to the tissues of upper fornix in the eyelid. The sutured artificial muscles can then be manipulated by the patient to transform between a contracted (open) position and a relaxed (closed) position via the use of eyedrops of different acidities.

Another surgical method includes piercing of active PAN fibers for the ptosis surgical procedure in which active PAN gel fibers are suture pierced under the eyelid through the bulbar conjunctiva in a serpentine manner so that a portion (e.g., one-half) of fiber thread length is under the conjunctiva and the remaining portion is out touching the cornea. An alternative ptosis surgical method comprises suture piercing active PAN gel fibers under the eyelid through the tarsal plates in a serpentine manner so that a portion (e.g., one-half) of thread length is under the conjunctiva and the remaining portion is out touching the cornea. The exposed parts of the PAN fiber react quicker to the pH environment in the eye.

The use of artificial muscles as implants in the human body are described in U.S. Pat. Nos. 6,168,575, 6,464,655, 6,511,508, 6,589,198, and 6,682,500, each of which is incorporated by reference in its entirety for all purposes.

Ionic polymeric artificial muscles and, in particular, contractile artificial muscles are described in the following references, each of which is incorporated by reference in its entirety for all purposes: M. Shahinpoor, K. J. Kim and Mehran Mojarrad, "Ionic Polymeric Conductor Composite Artificial Muscles," ERI/AMRI Press, Albuquerque, N. Mex., 2nd. Edition, (2005); M. Shahinpoor, "Ionic Polymer Conductor Composite Materials as Distributed Nanosensors, Nanoactuators and Artificial Muscles—A Review", Proceedings of the Second World Congress On Biomimetics and Artificial Muscle (Biomimetics and Nano-Bio 2004), Dec. 5-8, 2004, Albuquerque Convention Center, Albuquerque, N. Mex., USA, (2004); M. Shahinpoor, "Ionic Polymer Conductor Composites As Distributed Nanosensors, Nanoactuators and Artificial Muscles—A Review of Recent Findings", Proceeding of The International Conference on Advanced Materials and Nanotechnology, AMN-1, The MacDiarmid Institute for Advanced Materials and Nanotechnology, 9-11 Feb. 2003, Wellington, New Zealand, pp. 14-22, (2003); M. Shahinpoor, et al, "Soft Actuators and Artificial Muscles", U.S. Pat. No. 6,109,852, issued Aug. 29, 2000; M. Shahinpoor, et al, "Ionic Polymer Sensors and Actuators", U.S. Pat. No. 6,475,639, issued Nov. 5, 2002; M. Shahinpoor, "Artificial Muscles", Chapter in Encyclopedia of Biomaterials and Biomedical Engineering, edited by G. Wnek and G. Bowlin, Marcel Dekker Publishers, New York, N.Y., (2004); M. Shahinpoor and A. Guran, "Ionic Polymer-Conductor Composites (IPCC) as Biomimetic Sensors, Actuators and Artificial Muscles, SELECTED TOPICS IN STRUCTRONICS AND MECHATRONIC SYSTEMS, Editors: A. Belyaev and A. Guran, pp. 417-436, World Scientific Publishers, London, (2003); M. Shahinpoor, "Ionic Polymer-Conductor Composites As Biomimetic Sensors, Robotic Actuators and Artificial Muscles—A Review", Electrochimica Acta, Vol. 48, No. 14-16, pp. 2343-2353, (2003); K. J. Kim and M. Shahinpoor, "Application of Polyelectrolytes in Ionic Polymeric Sensors, Actuators, and Artificial Muscles", Review Chapter in Handbook of Polyelectrolytes and their Applications, edited by S. K. Tripathy, J. Kumar and H. S. Nalwa, vol. 3; Applications of Polyelectrolytes and Theoretical Models, American Scientific Publishers, Stevenson Ranch, Calif., USA (2002); K. J. Kim and M. Shahinpoor, "A Novel Method of Manufacturing Three-Dimensional Ionic Polymer-Metal Composites (IP-MC's) Biomimetic Sensors, Actuators and Artificial Muscle," Polymer, Vol. 43/3, pp. 797-802 (2002); M. Shahinpoor and K. J. Kim, "Novel Ionic Polymer-Metal Composites Equipped with Physically-Loaded Particulate Electrode As Biomimetic Sensors, Actuators and Artificial Muscles", Actuators and Sensors A, Physical, 96 (2/3) A, 3163, pp. 125-132, (2002); M. Shahinpoor, Y. Bar-Cohen, J. Simpson and J. Smith, "Ionic Polymer-Metal Composites (IPMC's) As Biomimetic Sensors, Actuators and Artificial Muscles—A Review", Smart Materials & Structures Int. Journal, vol. 7, pp. R15-R30, (1998); and M. Shahinpoor, M., "Active Polyelectrolyte Gels As Electrically-Controllable Artificial Muscles and Intelligent Network Structure", Book Chapter in Structronic Systems, Part II, edited by: H. S. Tzou, A. Guran, U. Gabbert, J. Tani and E. Breitbach, World Scientific Publishers, London, pp. 31-85, (1998).

As stated above, the present disclosure provides artificial muscles that can be implanted into the eyelid and sutured so as to allow for the correction of ptosis. The implanted artificial muscles can be formed from a highly resilient biocompatible silicone or other medical grade rubber and/or may include or be formed from a fibrous polyacrylonitrile (PAN) hydrogel. PAN hydrogel is a multiblock copolymer that is formed from a combination of hard blocks (nitrile groups) and soft blocks (hydrophilic groups), the proportion of which can be changed to modify the physical properties. PAN hydrogels have good biocompatibility and low toxicity. Compared with other hydrogels, PAN hydrogels have high tear strength. The FDA approved a hydrogel form of PAN in 2002 for a number of medical uses including cervical dilation during childbirth and gastro esophageal reflux disease (GERD).

Contractile fibrous gels of PAN artificial muscles are described in U.S. Pat. No. 5,389,222 as well as the references cited below, each of which is incorporated by reference in its entirety for all purposes: K. J. Kim, K. Choe, R. Samathan, J. Nam, M. Shahinpoor and J. Adams, "Toward Nanobiomimetic Muscles: Polyacrylonitrile Nanofibers", Proceeding of SPIE 11th Annual International Symposium on Smart Structures and Materials, 14-18 Mar. 2004, San Diego, Calif., SPIE Publication No. 5385-62, pp. 33-43, (2004); K. J. Kim, J. Caligiuri and M. Shahinpoor, "Contraction/Elongation Behaviour of Cation-Modified Polyacrylonitrile Fibers", Proceeding of SPIE 10th Annual International Symposium on Smart Structures and Materials, 2-6 Mar. 2003, San Diego, Calif., SPIE Publication No. 5051-23, pp. 207-213, (2003); K. J. Kim and M. Shahinpoor, "Electrical Activation of Contractile Polyacrylonitrile (PAN)-Conductor Composite Fiber Bundles As Artificial Muscles", Proceedings of the First World Congress On Biomimetics and Artificial Muscle (Biomimetics 2002), Dec. 9-11, 2002, Albuquerque Convention Center, Albuquerque, N. Mex., USA, (2002); M. Shahinpoor and M. Ahghar, "Modeling of Electrochemical Deformation in Poly-acrylonitrile (PAN) Artificial Muscles", Proceedings of the First World Congress On Biomimetics and Artificial Muscle (Biomimetics 2002), Dec. 9-11, 2002, Albuquerque Convention Center, Albuquerque, N. Mex., USA, (2002); K. J. Kim, J. Caligiuri, K. Choi, M. Shahinpoor, I. D. Norris, B. R. Mattes "Polyacrylonitrile Nanofibers as Artificial Nano-Muscles", Proceedings of the First World Congress On Biomimetics and Artificial Muscle (Biomimetics 2002), Dec. 9-11, 2002, Albuquerque Convention Center, Albuquerque, N. Mex., USA, (2002); M. Shahinpoor, K. J. Kim, L. O. Sillerud, I. D. Norris, B. R. Mattes, "Electroactive Polyacrylonitrile Nanofibers as Artificial Nanomuscles", Proceeding of SPIE 9th Annual International Symposium on Smart Structures and Materials, San Diego, Calif., SPIE Publication No. 4695-42, (March, 2002); M. Shahinpoor, K. J. Kim, and H. B. Schreyer, "Artificial Sarcomere and Muscle Made with Conductive Polyacrylonitrile (C-PAN) Fiber Bundles", Proceedings of SPIE 7th International Symposium on Smart Structures and Materials, Newport Beach, Calif., Vol. 3687, pp. 243-251 (March, 2000); H. B. Schreyer, N. Gebhart, K. J. Kim, and M. Shahinpoor, "Electric Activation of Artificial Muscles Containing Polyacrylonitrile Gel Fibers", Biomacromolecules, Vol. 1, No. 4, pp. 642-647, (2000); H. Brett Schreyer, Mohsen Shahinpoor, Kwang Kim, "Electrical activation of PAN Artificial Muscles", Proc. SPIE Smart Materials and Structures Conference, Mar. 1-5, 1999, New Port Beach, Calif., Publication No. SPIE 3669-19, pp. 192-198. (1999); M. Shahinpoor, "Active Polyelectrolyte Gels as Electrically-Controllable Artificial Muscles and Intelligent Network Structures", Book Chapter, in Active Structures, Devices and Systems, edited by H. S. Tzou, G. L. Anderson and M. C. Natori, World Science Publishing, Lexington, Ky., (1997); Salehpoor, K., Shahinpoor, M. and Mojarrad, M., "Some Experimental Results On The Dynamic Performance of PAN Muscles", Smart Materials Technologies, SPIE Publication No. Vol. 3040, pp. 169-173, (1997); K. Salehpoor, M. Shahinpoor and M. Mojarrad, "Electrically Controllable Artificial PAN Muscles", Proc. SPIE 1996 North American Conference on Smart Structures and Materials, Feb. 27-29, 1996, San Diego, Calif., vol. 2716, paper no. 07, (1996); See also, Y. Pierre Gobin, MD, Fernando Viñuela, MD, Harry V. Vinters, MD, Cheng Ji, MD and Kira Chow, MD, "Embolization with Radiopaque Microbeads of Polyacrylonitrile Hydrogel: Evaluation in Swine", Radiology, vol. 214, pp. 113-119, January (2000) and, Va Stoy, "New type of hydrogel for controlled drug delivery", J Biomater Appl., vol. 3, No. 4, pp. 552-604, April (1989).

According to one embodiment, the implanted artificial muscles can transform between multiple positions or operating modes. Transformation can be activated via a biasing means. According to this embodiment, the biasing means allows the patient to selectively shift eyelid position from a first position or operating mode to a second position or operating mode. For example, the first position or operating condition can be a contracted, or open, position. In this position, it may be desirable that the strength of contraction of the artificial muscles by the biasing means is less than the strength of the contractile fibers in the eye, so as to allow for blinking. The second position or operating condition may be a relaxed, or closed position. The biasing means can be, for example, a chemical solution. Moreover, the chemical solution may be provided in eye drop form.

Accordingly, the implanted artificial muscles can be chemically-activated. For example, the implanted artificial muscles may be formed from a chemically activated fibrous PAN hydrogel. As a non-limiting example, the artificial muscle fibers can be formed from a pH active material such as a pH active hydrogel form of fibrous PAN artificial muscles. The pH active artificial muscles can be implanted such that different muscular behavior can be achieved when the muscles are stimulated with solutions containing different pH levels. For example, according to one method, upon using a mildly acidic solution such as an eye drop having a pH of around 4, an example of which is Ciloxan® ophthalmic solution (Alcon labs, Fort Worth, Tex.), the PAN muscles contract and draw the eyelid open by providing the necessary resilient contraction force in tension to overcome the weight of the eyelid and draw the eyelid open. The natural muscles of eye closure or the orbicularis muscle are, however, sufficiently strong to overcome the artificial muscle tension and resiliency thereby stretching the highly resilient and compliant PAN muscle fibers and closing the eye so as to provide normal blinking function. A mildly alkaline solution, such as an eye drop with a pH of around 8, an example of which is a Timolol® solution, will, in turn, enable the PAN muscle fibers to expand and relax to allow the eye to remain closed for sleep or at other desired times. The biocompatible contractile PAN artificial muscles generally have two distinct resilience coefficients or moduli of elasticity in contraction and in expansion, respectively, upon pH activation as reported in the following papers: M. Shahinpoor, K. J. Kim, and H. B. Schreyer, "Artificial Sarcomere and Muscle Made with Conductive Polyacrylonitrile (C-PAN) Fiber Bundles", Proceedings of SPIE 7th International Symposium on Smart Structures and Materials, Newport Beach, Calif., Vol. 3687, pp. 243-251 (March, 2000); H. B. Schreyer, N. Gebhart, K. J. Kim, and M. Shahinpoor, "Electric Activation of Artificial Muscles Containing Polyacrylonitrile Gel Fibers", Biomacromolecules, Vol. 1, No. 4, pp. 642-647, (2000); M. Shahinpoor, K. J. Kim and Mehran Mojarrad, "Ionic Polymeric Conductor Composite Artificial Muscles," ERI/AMRI Press, Albuquerque, N. Mex., 2nd. Edition, (2005); each of which is incorporated herein by reference.

Figure 2A:
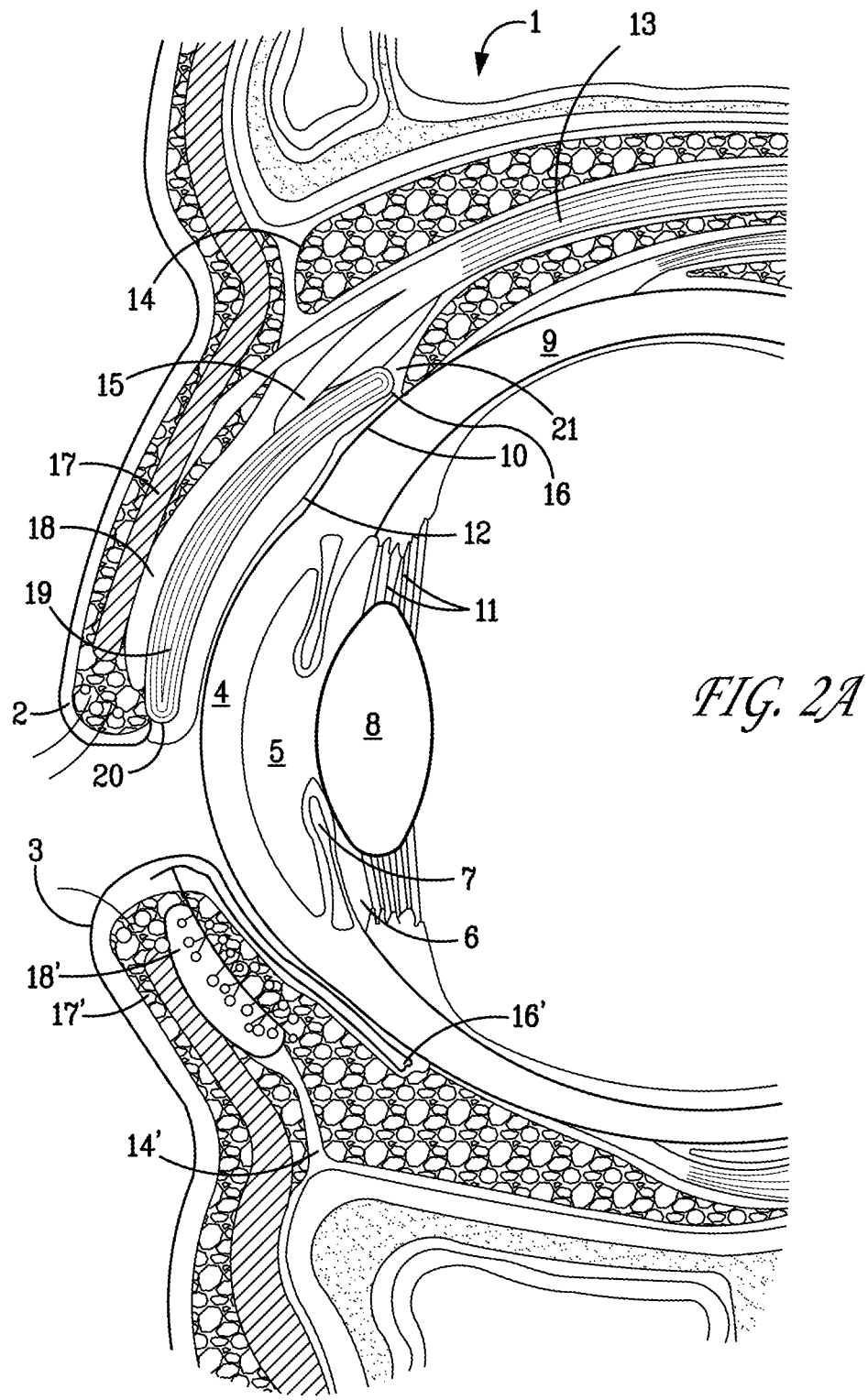
FIGS. 2A and 2B are schematic zoomed-in cross sectional views through the eye of a patient showing the relative implanted position of PAN artificial muscle fibers of the present invention for restoring eyelid function in an expanded relaxed (A) or a contracted (B) configuration.
Figure 2B:
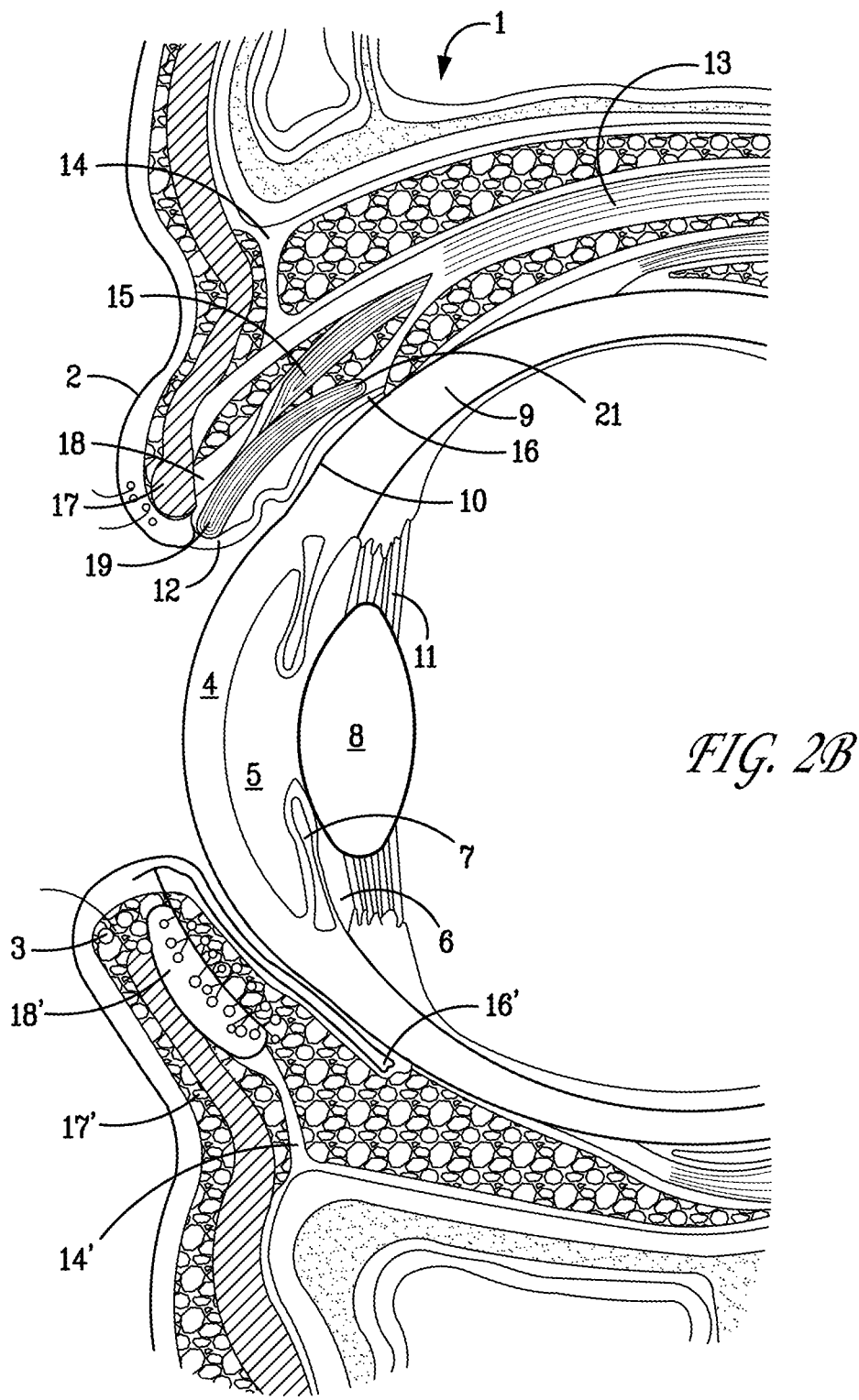

FIGS. 2A and 2B are schematic zoomed-in cross sectional views through the eye of a patient showing the relative implanted position of PAN artificial muscle fibers 19 for restoring eyelid function in an expanded relaxed (FIG. 2A) or a contracted (FIG. 2B) configuration. In FIGS. 2A and 2B the eye anatomy is denoted by 1 where the upper eyelid 2 and the lower eyelid 3 are such that the upper eyelid 2 is drooping in the presence of levator palpebrae superioris muscle 13, the orbital septums 14 and 14', the superior tarsal (Muller's) muscle 15, the superior conjunctival fornix 16, the inferior conjunctival fornix 16', the orbicularis oculi muscles 17 and 17', the superior tarsus 18, the inferior tarsus 18', the sclera 9, the bulbar conjunctiva 10, the superior palpebral conjunctiva 12, the zonules 11, the cornea 4, the crystalline lens 8, the anterior chamber 5, the iris 7, and the posterior chamber 6.

As shown, the implanted contractile artificial muscle fibers 19 are sutured under the superior palpebral conjunctiva in a serpentine and parallel configuration with respect to tarsal (meibomian) glands of the eyelid and suture anchored to the tissues of upper superior fornix 21 and the lower edge of the eyelid 20. The serpentine-sutured contractile artificial muscle fiber diameter can be about 100 microns in overall diameter and can be composed of strands of about 10 microns in diameter.

In FIG. 2A the contractile muscle fibers 19 are in a relaxed and expanded state while in FIG. 2B the contractile fibrous muscles are in a contracted state. According to one method, the sutured implanted eye drop activated PAN resilient contractile artificial muscles can be such that they provide a resilient force in tension in the range of 0 to a few 10's of grams. Accordingly, the sutured implanted artificial muscles upon activation with one or more chemical stimulants can have a range of deformation of about 20 mm between contraction and expansion.

As stated before, the chemical stimulants can take the form of solutions have different chemical properties such as differing pH levels. For example, an acidic eye drop solution can be used to penetrate the superior palpebral conjunctiva and contract the polymeric artificial muscle fibers. The contractile fibers are so resilient that they allow the blinking or closing of the eyelid by the powerful orbicularis oculi muscles. In contrast, an alkaline eye drop can penetrate through the superior palpebral conjunctiva and cause the polymeric muscles to relax and expand so that the eye lid can easily close with minimum effort when the patient desires to close his or her eyes for extended periods of time. The effort required for eye lid closure is particularly reduced when the sympathetic Muller's muscles relax right before a person falls asleep. According to one embodiment, the acidic solution may have a pH level of around 4 and the alkaline solution may have a pH level of around 8. It will be understood that additional chemical solutions including, but not limited to, chemical solutions having different pH levels can be used and that the present disclosure encompasses solutions having the appropriate chemical property required to stimulate movement of the artificial muscles in an appropriate and/or desired way.

Figure 3A:
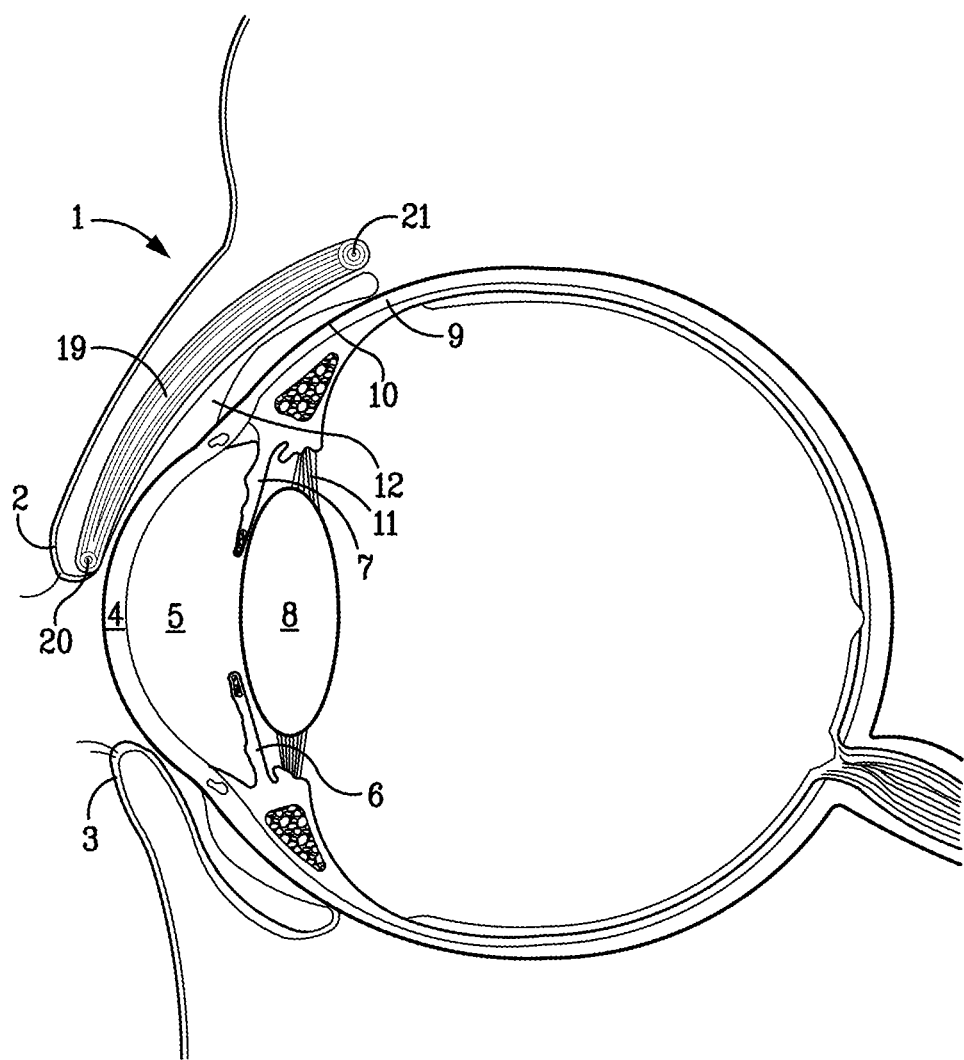
FIGS. 3A and 3B are schematic zoomed-out cross sectional views through the eye of a patient showing the relative implanted position of PAN artificial muscle fibers of the present invention for restoring eyelid function in an expanded relaxed (A) or a contracted (B) configuration.
Figure 3B:
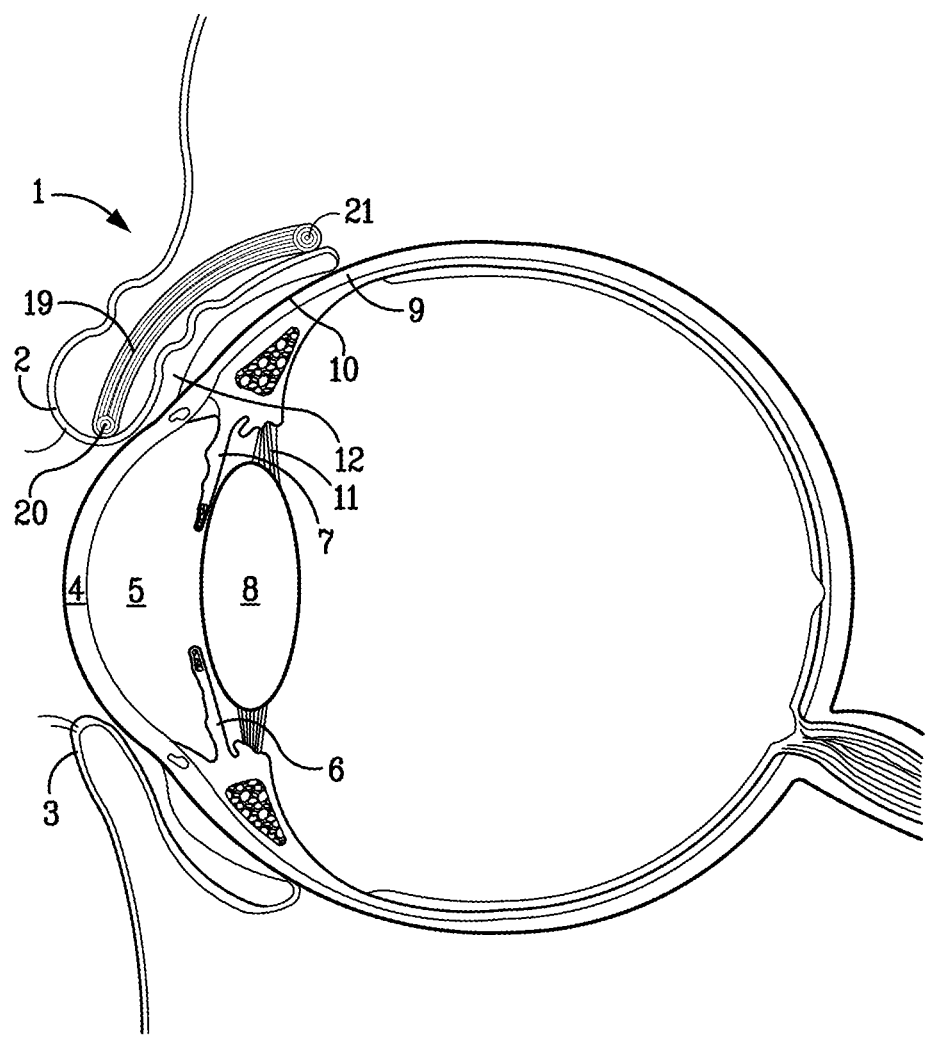

Turning now to FIGS. 3A and 3B, the eye anatomy is denoted by 1 where the upper eyelid 2 and the lower eyelid 3 are such that the upper eyelid 2 is drooping in the presence of the sclera 9, the bulbar conjunctiva 10, the superior palpebral conjunctiva 12, the zonules 11, the cornea 4, the crystalline lens 8, the anterior chamber 5, the iris 7, the posterior chamber 6. As shown, the implanted contractile artificial muscle fibers 19 are sutured under the superior palpebral conjunctiva in a serpentine and parallel configuration with respect to tarsal (meibomian) glands of the eyelid and suture anchored to the tissues of upper superior fornix 21 and the lower edge of the eyelid 20. In FIG. 3A the contractile muscle fibers 19 are in a relaxed and expanded state while in FIG. 3B the contractile fibrous muscles are in a contracted state. Again, the contractile fibers are so resilient that they allow the blinking of the eyelid or closing of the eyelid by the orbicularis oculi muscles.

Figure 4:
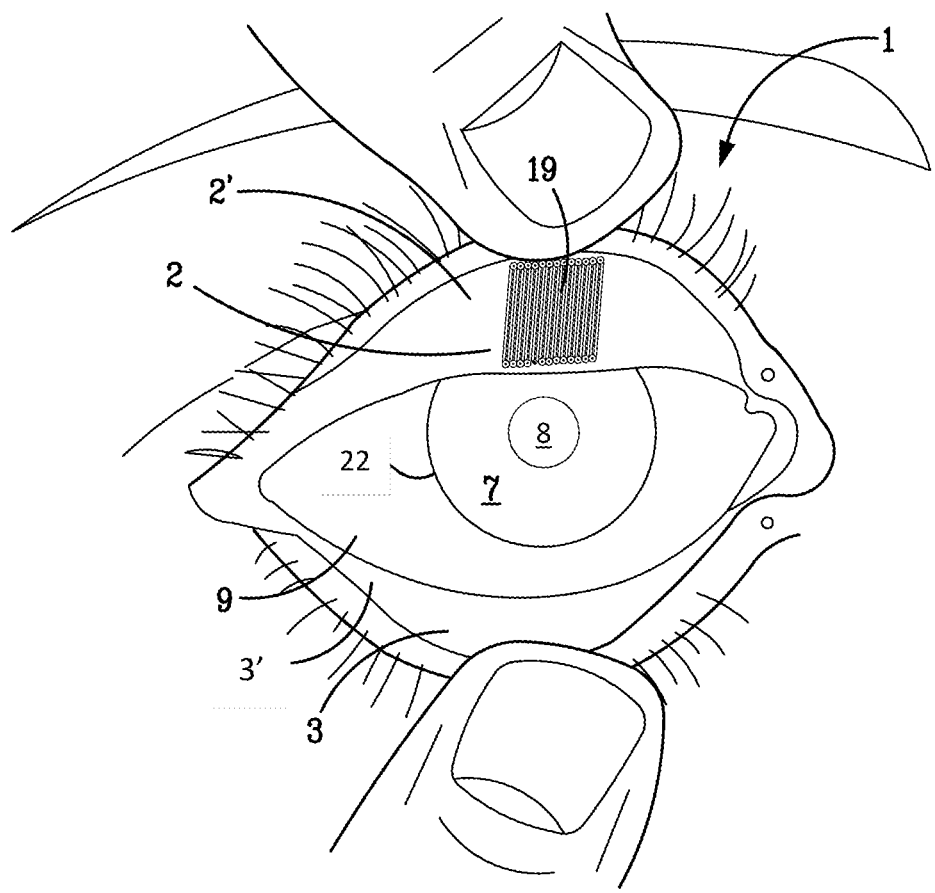
FIG. 4 is a schematic front view of the eye of a patient showing the tarsal glands and relative implanted position of PAN artificial muscle fibers of the present invention for restoring eyelid function.

FIG. 4 is a schematic front view of the eye of a patient 1 showing the upper eyelid 2 and the lower eyelid 3 are such that the upper eyelid 2 is flipped backward to see the upper and lower tarsal gland 2' and 3' in the presence of the sclera 9, the limbus 22, the crystalline lens 8, and the iris 7. As shown, the implanted contractile artificial muscle fibers 19 are sutured under the superior palpebral conjunctiva in a serpentine and parallel configuration with respect to tarsal (meibomian) glands of the eyelid and suture anchored to the tissues of upper superior fornix 21 and the lower edge of the eyelid 20.

A surgical method for restoring eyelid function in a ptosis patient comprises suture anchoring an artificial muscle network to the superior palpebral conjunctiva tissues in a serpentine configuration with respect to tarsal glands of the eyelid, and suture anchoring the artificial muscle network to the tissues of the upper orbital septum. The artificial muscle network can be sutured such that the orbicularis muscle can bias the eyelid to closed position. The artificial muscle network can be responsive to one or more biasing forces. The artificial muscle network can be configured to contract, and therefore open the eyelid, in response to a first biasing force. The artificial muscle network can be configured to relax, and therefore close the eyelid, in response to a second biasing force. The first and second biasing forces can be chemical solutions.

Another surgical method for restoring eyelid function in a ptosis patient comprises a ptosis surgical procedure in which an active artificial muscle network (e.g., active PAN gel fibers) is suture pierced under the eyelid through the bulbar conjunctiva in a serpentine manner so that a portion (e.g., one-half) of fiber thread length is under the conjunctiva and the remaining portion is out touching the cornea. An alternative ptosis surgical method comprises suture piercing active PAN gel fibers under the eyelid through the tarsal plates in a serpentine manner so that a portion (e.g., one-half) of thread length is under the conjunctiva and the remaining portion is out touching the cornea. The exposed parts of the PAN fibers react quicker to the pH environment in the eye.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide an illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

Unless specifically stated to the contrary, all references cited in the present disclosure are incorporated by reference in their entirety for all purposes.

What is claimed is:

1. A method for restoring eyelid function in a ptosis patient, comprising:
  (a) suture anchoring an artificial muscle network to superior palpebral conjunctiva tissues in a serpentine configuration with respect to tarsal glands of the eyelid; and
  (b) suture anchoring the artificial muscle network to tissues of upper orbital septum;
  (c) wherein the artificial muscle network comprises a chemically active biocompatible hydrogel form of polyacrylonitrile (PAN) fibers;
  (d) wherein the artificial muscle network contracts so as to bias the eyelid into a first open position in response to activation of a first biasing force by a mildly acidic solution having a pH around 4 or higher;
  (e) wherein the artificial muscle network relaxes so as to bias the eyelid into a second closed position in response to activation of a second biasing force by a mildly alkaline solution having a pH around 8 or lower.

2. The method of claim 1, wherein approximately half of thread length of the fibers is under the conjunctiva and the other approximately half of the thread length of the fibers is out touching the cornea.

3. A method for restoring eyelid function in a ptosis patient, comprising:
   (a) suture anchoring an artificial muscle network to superior palpebral conjunctiva tissues in a serpentine configuration with respect to tarsal glands of the eyelid; and
   (b) suture anchoring the artificial muscle network to tissues of upper orbital septum;
   (c) wherein the artificial muscle network comprises a highly resilient biocompatible silicone or other medical grade rubber;
   (d) wherein the artificial muscle network contracts so as to bias the eyelid into a first open position in response to activation of a first biasing force by a mildly acidic solution having a pH around 4 or higher;
   (e) wherein the artificial muscle network relaxes so as to bias the eyelid into a second closed position in response to activation of a second biasing force by a mildly alkaline solution having a pH around 8 or lower.

4. The method of claim 3, wherein approximately half of thread length of the fibers is under the conjunctiva and the other approximately half of the thread length of the fibers is out touching the cornea.

5. The method of claim 3, wherein the artificial muscle network is sutured such that orbicularis muscle biases the eyelid to closed position.

6. The method of claim 3, wherein the artificial muscle network comprises a chemically active biocompatible hydrogel form of polyacrylonitrile (PAN) fibers.

7. The method of claim 3, wherein the mildly acidic solution has a pH between around 4 and 7.

8. The method of claim 3, wherein the mildly alkaline solution has a pH between 7 and around 8.

9. The method of claim 3, wherein the mildly acidic solution has a pH of around 4.

10. The method of claim 3, wherein the mildly alkaline solution has a pH of around 8.

* * * * *